United States Patent [19]

Reischl et al.

[11] 4,454,259

[45] Jun. 12, 1984

[54] PROCESS FOR THE PREPARATION OF POLYADDITION PRODUCTS OF ISOCYANATES AND DENATURED BIOMASSES, THEIR USE AS REACTIVE FILLERS AND AS PLANT NUTRIENTS AND A PROCESS FOR THE PRODUCTION OF SHEETS OR SHAPED ARTICLES USING THE POLYADDITION PRODUCTS

[75] Inventors: Artur Reischl; Kuno Wagner, both of Leverkusen, Fed. Rep. of Germany

[73] Assignee: Bayer Aktiengesellschaft, Leverkusen, Fed. Rep. of Germany

[21] Appl. No.: 480,536

[22] Filed: Mar. 30, 1983

Related U.S. Application Data

[62] Division of Ser. No. 146,859, May 5, 1980, Pat. No. 4,393,166.

[30] Foreign Application Priority Data

May 21, 1979 [DE] Fed. Rep. of Germany ....... 2920525

[51] Int. Cl.$^3$ .................. C02F 11/14; C08L 61/20; C08L 61/32; C05C 9/00; C08F 8/28
[52] U.S. Cl. .................. 523/129; 523/132; 525/54.1; 526/238.1; 528/1; 435/177; 435/181; 435/182; 210/631; 210/757; 210/764; 210/927; 210/928; 71/12; 71/13; 71/14; 71/15; 71/16; 71/19; 71/25; 71/28
[58] Field of Search .............. 523/129, 132, 200; 525/54.1; 526/238.1; 528/1; 252/1; 524/442; 435/174, 177, 181, 182, 253, 255, 804; 210/631, 751, 757, 764, 927, 928, DIG. 15; 71/12, 13, 14, 15, 16, 19, 25, 27, 28, 30, 58

[56] References Cited

U.S. PATENT DOCUMENTS

| | | | |
|---|---|---|---|
| 3,574,062 | 4/1971 | Sato | 195/63 |
| 3,672,955 | 6/1972 | Stanley | 195/68 |
| 3,705,084 | 12/1972 | Reynolds | 195/63 |
| 3,791,927 | 2/1974 | Forgione et al. | 195/63 |
| 3,812,618 | 5/1974 | Wood et al. | 47/56 |
| 3,812,619 | 5/1974 | Wood et al. | 47/58 |
| 3,905,920 | 9/1975 | Botcharoff | 250/536 |
| 3,929,575 | 12/1975 | Miescher | 195/30 |
| 3,950,222 | 4/1976 | Takasaki | 195/68 |
| 3,976,465 | 8/1976 | O'Donnell | 71/13 |
| 4,021,368 | 5/1977 | Nemec et al. | 252/427 |

FOREIGN PATENT DOCUMENTS

| | | |
|---|---|---|
| 2208644 | 8/1973 | Fed. Rep. of Germany . |
| 1272044 | 12/1961 | France . |
| 1517813 | 7/1978 | United Kingdom . |
| 1541100 | 2/1979 | United Kingdom . |

*Primary Examiner*—John Kight, III
*Assistant Examiner*—Nathan M. Nutter
*Attorney, Agent, or Firm*—Gene Harsh; Joseph C. Gil; Lyndanne M. Whalen

[57] ABSTRACT

The instant invention is directed to a process for the production of denatured polyaddition products of biomasses and isocyanates, comprising reacting (A) from 5 to 98%, by weight, based on (A)+(B), of a biomass based on microorganisms or derivative and decomposition products thereof with (B) from 95 to 2%, by weight, based on (A)+(B), of a compound containing isocyanate groups, at temperatures of at least 50° C. with complete denaturing of component (A).

7 Claims, No Drawings

PROCESS FOR THE PREPARATION OF POLYADDITION PRODUCTS OF ISOCYANATES AND DENATURED BIOMASSES, THEIR USE AS REACTIVE FILLERS AND AS PLANT NUTRIENTS AND A PROCESS FOR THE PRODUCTION OF SHEETS OR SHAPED ARTICLES USING THE POLYADDITION PRODUCTS

This application is a division, of application Ser. No. 146,859 filed May 5, 1980, now U.S. Pat. No. 4,393,166.

BACKGROUND OF THE INVENTION

This invention relates to a process for irreversibly denaturing and, at the same time, deodorizing biomasses containing microorganisms and the secondary products thereof, particularly biological clarified sludges, by reaction with compounds containing isocyanate groups. According to the present invention, the thus-obtained substantially odorless, denatured polyaddition products are used as reactive fillers or molding compositions in the production of plastics or as long-term fertilizers in agriculture.

In biological purification plants, organochemical effluent impurities are degraded, i.e. biologically eliminated, by means of microorganisms. Under the conditions applied, the microorganisms multiply to a particularly marked extent. The quantity of the biomass consists mainly of bacteria in the so-called "activated sludge basin" of the purification plant increasing daily by from about 3 to 4%, by weight, so that, although some of the microorganisms die, the quantity of bacteria would double in from 3 to 4 weeks. Accordingly, some of the biomass has to be continuously removed from the activated sludge basin in the form of so-called "surplus activated sludge" in order to maintain the optimal conditions for microbial effluent purification. For this reason, biomasses accumulate worldwide in extremely large and ever-increasing quantities in the fully biological purification of industrial and communal effluents. In the Federal Republic of Germany alone, about 2 million metric tons (expressed as dry weight) per year of these protein-containing biomasses are at present either being dumped or burned. Even today, the necessary removal of the water from the activated sludges is still a problem because, under the sedimentation conditions normally applied in the purification plants, the activated sludge to be removed contains only about 1%, by weight, of microbial dry mass. In conventional centrifuges, the solids content of the sludge may only be concentrated to from 7 to 9%, by weight. Even where polyelectrolytes are added and centrifugal decanters used, it may only be increased to from 12 to 15% by weight.

Even in these low concentrations, the activated sludges have a pronounced gel structure and a relatively high viscosity on account of the pronounced chemical and physical binding of the water to the microorganisms. For this reason, normal filtration is impossible without certain treatment. Filtration is also complicated by the fact that the bacteria cells attract one another and form common, slimy shells, resulting in the formation of tacky flakes. In practice, therefore, inorganic primary sludges are added to the surplus activated sludges in from substantially the same to twice the quantity in order to facilitate removal of the water on an industrial scale by means of filter presses. In this way, a filter cake having a very high content of inorganic constitutents and a water content of about 50%, by weight, based on the mass as a whole, is obtained. On the other hand, burning may only be carried out using surplus activated sludge powders having a very high content of organic mass. This is done either under substantially anhydrous conditions with the disadvantage that the drying process requires far more energy than may be obtained as heat equivalent during burning, or aqueous activated sludge is burned with an addition of, for example, heavy oil as energy carrier in a quantity sufficient to evaporate the quantities of water entrained.

Another problem is that, as soon as it is isolated from the settling basin, the excess bacterial sludge immediately begins to rot and gives off an unbearable odor. Even anhydrous activated sludge powder dried at 110° C. has a very unpleasant odor and continues to rot on becoming moist. The presence of pathogenic germs cannot be ruled out.

For these reasons, the composting of the treated sludge or its direct use as a fertilizer in agriculture is possible only to a limited extent. The elimination and utilization of treated sludges involve considerable ecological problems which have not been solved in a satisfactory manner. Known processes for working-up biomasses of microorganisms and the disadvantages and inadequacies thereof are discussed in detail in U.S. patent application Ser. No. 84,002, now abandoned.

According to the estimates of the Federal Ministry of the Interior of the Federal Republic of Germany (1975 Waste Economy Program of the Federal Government; Environmental Letter 13, 1976), the annual accumulation of treated sludge will have increased by 1985 to about 50 million cubic meters from communal plants plus another 30 million cubic meters from industrial plants, which for a water content of 95% represents approximately 4 million metric tons of dry purified sludge per year. Accordingly, it is urgently necessary both for ecological reasons and also for economic reasons to find improved processes for working up surplus activated sludges with elimination of harmful impurities. It is also necessary to enable the purified sludges consisting mainly of high-quality proteins, nucleic acids enzymes and other valuable organic compounds to be utilized without endangering the environment by recycling on an industrial scale.

It has now surprisingly been found that various biomasses based on microorganisms or metabolism and/or decomposition products thereof, including in particular the above-described purified sludges from biological purification plants, may be worked-up in a simple and considerably improved manner. This is accomplished by reacting the biomasses with compounds containing isocyanate groups. The reaction may take place optionally in the presence of organic solvents, carbonyl compounds, compounds capable of aminoplast or phenoplast formation and/or other additives, optionally at elevated temperature and/or elevated pressure. In the context of the present invention "working-up" is to be understood to mean that the biomasses are concentrated, irreversibly deodorized and, in this way, made available for utilization in the plastics-processing industry and in agriculture. The biomass polyaddition products obtained in accordance with the present invention are sterile, completely odorless in most cases and contain the biomass used in chemically bound and completely denatured form. The products are not tacky in aqueous phase, may be filtered without difficulty and dried in energy-saving manner. They are completely stable in storage and free from pathogenic organisms.

The total enzyme deactivation and complete cell death of the biomasses completely suppress decomposition and putrefaction processes, fermentation and unpleasant odor formation of enzymatically or microbiologically degradable cell ingredients. Accordingly, the process products may be indefinitely stored both in dry and also in moist form without giving off unpleasant odors and without undergoing further enzymatic degradation.

It is known that isocyanates may be reacted with other starting materials of the type commonly encountered in polyurethane chemistry in the presence of biologically active substances to form high molecular weight compounds. In contrast to the present invention, whose object is to denature biomasses based on microorganisms with complete destruction of living cells and active enzymes present therein, the known processes seek to fix selected biologically active compounds in polyurethanes with full retention of the bioactivity.

Thus, in German Offenlegungsschriften Nos. 2,612,138 and 2,625,544, for example, describe the fixing of enzymes, antigens, antibodies or antibiotics by means of prepolymers containing isocyanate groups. In this case, the polyaddition reaction has to be carried out very carefully to avoid destruction of the bioactive substances. The thus obtained products are used as biospecific catalysts, antigens or antibodies. Various biologically fully active or even activated substances fixed to a polyurethane matrix may be similarly produced in accordance with German Offenlegungsschriften Nos. 2,319,706 and 2,625,471 and U.S. Pat. Nos. 3,574,062; 3,705,084; 3,791,927; 3,672,955; 3,929,575; and 3,905,920. As mentioned above, the process according to the present invention differs from these known processes not only in regard to the starting materials used (microbial biomasses of extremely heterogeneous composition which still contain virtually all the cell constituents and, in general, even have a largely undamaged cell structure and also contain living cells are used instead of isolated biochemically active individual compounds), but also in regard to the reaction conditions so that the biomasses treated in accordance with the present invention are completely changed physically, chemically and biologically in relation to the starting material.

DESCRIPTION OF THE INVENTION

Accordingly, the present invention relates to a process for the preparation of denatured polyaddition products of biomasses and isocyanates, comprising reacting (A) from 5 to 98%, by weight, preferably from 20 to 90%, by weight, based on (A)+(B), of a biomass based on microorganisms or derivative and decomposition products thereof; with (B) from 95 to 2%, by weight, preferably from 80 to 10%, by weight based on (A)+(B), of a compound containing isocyanate groups; optionally in the presence of (C) water and/or an organic solvent; and optionally in the presence of (D) organic and/or inorganic additives; at temperatures of at least 50° C., preferably from 50° to 200° C., and, with particular preference, from 80° to 150° C., and are thus completely denatured.

In one particular embodiment of the present process, condensation reactions may be carried out with the biomasses before, after or during the isocyanate polyaddition reaction. This may be done optionally with partial hydrolytic decomposition of the biomasses, by reacting them with suitable carbonyl compounds, particularly aldehydes or compounds capable of aminoplast and/or phenoplast formation.

In the context of the present invention, "biomasses" are understood to be various biosystems of microorganisms, such as prokaryontae and eurkaryontae, for example bacteria, yeasts, protozoae and other single-cell microorganisms, fungi, algae, etc., which are present in the divided state, dormant state, in a state of partial or complete cell death or which are already in the process of enzymatic decomposition or decomposition by foreign cultures.

Examples of such biosystems include biomasses of microorganisms or biological purification plants and other microbial or bacterial biomasses of the type which accumulate:

(a) in processes for recovering products of the primary metabolism, i.e., for example, in the biotechnical production of ethanol, butanol, acetone, citric acid, lactic acid, tartaric acid, simple aliphatic carboxylic acids, amino acids, etc.;

(b) in technical fermentation processes for the production of products of the secondary metabolism, for example in the production of antibiotics, vitamins, growth hormones, steroid hormones, alkaloids, etc.;

(c) in processes for recovering cell constituents, such as enzymes, nucleic acids or polysaccharides; and (d) in processes for producing yeast, for example for baking purposes, for alcoholic fermentation or for recovering proteins from methane, petroleum and methanol.

Biomasses of the type which accumulate in biotransformation processes include processes where microorganisms are used as catalysts for organochemical reactions, such as oxidation, reduction, decarboxylation, phosphorylation, amination, deamination, acetylation, de-acetylation, etc.

Biomasses preferably used in the process of the present invention are:

(a) Biomasses from biological plants for the purification of industrial and communal effluents. Such biomasses consist of numerous types of bacteria, algae and fungi which function optimally at a P:N:C ratio of about 1:5:100 and which are known as "omnivores". The biomasses emanating from purification plants, which are also known as "purified sludges" or "activated sludges", may be used in the process according to the present invention even when they contain traces of mercury, cadmium, zinc, iron, chromium and/or lead ions.

(b) Digested sludges and biosludges of various types and also biomasses containing large amounts of *Escherichia coli* and/or various suspended vegetable substances.

(c) Biomasses from anaerobic (intensive) digestion processes, refuse/purified sludge composting products. Examples include biomasses from thermophilic digestion processes (aerobic-thermophilic processes), products obtained by the aerobic composting of purified sludge by the quick-rotting process, microbially infested fibrous sludges, sludges from the food and luxury-food industries, for example sludges from dairies and abattoirs, and biosludges which have been dried and dumped.

(d) A variety of yeasts (fungi) from technical processes, for example from alcoholic fermentation processes.

(e) Biomasses from the production of acetic acid, lactic acid, citric acid or tartaric acid, also bacterial cultures fermenting by enzymatic processes.

(f) Defective parts of yeast cultures.

(g) Biomasses from the production of proteins based on various hydrocarbon sources, such as petroleum, paraffin cuts, methane or methanol. Particularly suitable biomasses of this type are biomasses based on certain yeast cells from industrial installations for the production of protein from petroleum fractions and defective parts of such biomasses. In this connection, particularly suitable biomasses are also biomasses of single-cell microorganisms consisting of bacterial mixed cultures, of the type used in the production of proteins from natural gas (methane). Other suitable biomasses are biomasses or pseudomonas bacteria which are cultivated in fermenters at about 37° C. and from which high-protein feeds may be produced using methanol as the carbon source.

(h) Biomasses from the production of penicillin, for example *Pencillium notatum* and *Pencillium chrysogenum*.

(i) Biomasses from the final stage of the production of tetracycline (*streptomycetes*), biomasses from filament-like bacteria from the production of sisomycin (*micromonospora*) and other types of streptomyces.

(j) Biomasses based on various other bacteria and fungi, of the type described in detail in U.S. patent application Ser. No. 84,002, now abandoned, and numerous other microbial biomasses of the type described in the literature (cf. Synthesis 4, 120–134 and 147–157 (1969)). These biomasses may consist of pure culture and of mixed cultures, i.e. of cultures which have been infected during fermentation processes and are therefore unuseable, and may contain, for example, even in admixture, dead cells of vegetable origin or cell ingredients, such as hemi-celluloses.

(k) Algae, such as blue algae, green algae (for example *chlorella*), diatoms, conjugatae, flagellar algae, brown algae and red algae, and also protozoate.

(l) Mixed cultures of various bacteria, fungi and algae and also cultures of biomasses which are infected with other types of fungi, bacteria, etc. and which have a complex composition. Examples of such mixed cultures are mixed cultures of the type grown on spent residues in the process of decomposition, nutrient media (such as gelatin, molasses, starches and other polysaccharides), in the open air and in moist form and also on protein-containing, still living or even already decomposing algae.

Mixtures of different biomasses may also be used in the process according to the present invention. The present process may also be used in cases where the biomasses contain a variety of different impurities. In this connection, reference is made by way of example to biomasses containing heavy metal salts, plant protection agents, antibiotics or other organic or inorganic chemicals.

It is particularly preferred to use the aqueous or dried powder-form purified sludges from industrial and communal purification plants described in detail above for the isocyanate polyadditon reactions according to the present invention. These purified sludges do not have a defined composition, but instead consist of many types of bacteria, fungi and protozae, depending on the contamination of the effluent and the biological conditions. Of these many types of bacteria, fungi and protozae, the following few are mentioned by way of example: *Aerobacter aerogenes, Corynebacterium laevaniformas, Paracolobactrum aerogenoides, Escheria intermedium, Escheria faecale*, Flavobacteria, Pseudomonas, Nitrosomonas and *Nitrobacter geni*, also *Shaerotilus natens* and white sulfur bacteria. In addition, enzymes, ferments and algae are also present.

The biomasses used in the process according to the present invention contain a variety of compounds containing H-acid groups which are capable of entering into polyaddition reactions with isocyanates (cf. for example "Handbuch der Frischwasser and Abwasserbiologie", Vol. II, page 620 (1960) by H. Lubmann). Examples of these compounds are inter alia proteins, (for example lipoproteins, glycoproteins) as constituents of enzymes; the enzymes themselves (such as glucose oxidase, catalase, glucose isomerase, invertase, lactase, naringinase, lipases, asparaginases, α-amylases and glycoamylases, cellulases, lysozymes, proteases, etc.); nucleoproteins; ribonucleic acids and deoxyribonucleic acids; phosphatides, (particularly inositol phosphatide, colamine cephalin and serine sephalin; lipoids or plasmalogens providing they contain colamine bound in the form of a phosphoric acid ester as base); sugars and polysaccharide-like cell reserve substances and cell ingredients, hemi-celluloses, starches, pectins and lignins: constituents of the cell walls of bacteria, for example, polymers of amino sugars (acetyl glucosamine+N-acetyl muramic acid) which are cross-linked by way of polypeptides in the N-acetyl muramic acid component; cell wall constituents of fungi and algae, (such as celluloses, hemi-celluloses and other polysaccharides) and chitine fractions with acetyl gluosamine and acetyl galactosamine fractions.

Component (B) in the process according to the present invention may in principle be formed by various low molecular weight or high molecular weight monoisocyanates or polyisocyanates which are liquid or soluble in an organic solvent at the processing temperatures. According to the present invention, however, it is also possible to use products containing isocyanate groups which are infusible or insoluble. For example, it is possible to use aliphatic, cycloaliphatic, araliphatic, aromatic and heterocyclic polyisocyanates of the type described, for example, by W. Siefken in Justus Liebigs Annalen der Chemie, 562, pages 75 to 136. Examples include those corresponding to the following general formula:

wherein
n=2 to 4, preferably 2; and
Q represents an aliphatic hydrocarbon radical containing from 2 to 18 carbon atoms, preferably from 6 to 10 carbon atoms, a cycloaliphatic hydrocarbon radical containing from 4 to 15, preferably from 5 to 10 carbon atoms, an aromatic hydrocarbon radical containing from 6 to 15 carbon atoms, preferably from 6 to 13 carbon atoms or an araliphatic hydrocarbon radical containing from 8 to 15 carbon atoms, preferably from 8 to 13 carbon atoms. Specific examples include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3-and 1,4-diisocyanate and mixtures of these isomers, 1-isocyanato-3,3,5-trimethyl-5-isocyanatomethyl cyclohexane (German Auslegeschrift No. 1,202,785 or U.S. Pat. No. 3,401,190), 2,4- and 2,6-hexahydrotolylene diisocyanate and mixtures of these isomers, hexahydro-1,3- and/or 1,4-phenylene diisocyanate, perhydro-2,4' and/or -4,4'-diphenyl methane diisocyanate, 1,3- and 1,4-phenylene diisocyanate, 2,4- and 2,6-tolylene diisocyanate and mixtures of these isomers, diphenyl methane-2,4' and/or -4,4'-diisocyanate and naphthylene-1,5-diisocyanate.

According to the present invention, it is also possible to use triphenyl methane-4,4',4"-triisocyanate; polyphenyl polymethylene polyisocyanates of the type obtained by condensing aniline with formaldehyde, followed by phosgenation (British Pat. Nos. 874,430 and 848,671); m- and p-isocyanatophenyl sulfonyl isocyanates (U.S. Pat. No. 3,454,606); perchlorinated aryl polyisocyanates (German Auslegeschrift No. 1,157,601 or U.S. Pat. No. 3,277,138); polyisocyanates containing carbodiimide groups (German Pat. No.1,092,007, U.S. Pat. No. 3,152,162 and German Offenlegungsschriften Nos. 2,504,400; 2,537,685; and 2,552,350); norbornane diisocyanates (U.S. Pat. No. 3,492,330); polyisocyanates containing allophanate groups (British Pat. No. 994,890, Belgian Pat. No. 761,626 and Dutch Patent Application No. 7,102,524); polyisocyanates containing isocyanurate groups (U.S. Pat. No. 3,001,973, German Pat. Nos. 1,022,789; 1,222,067; and 1,027,394 and German Offenlegungsschriften Nos. 1,929,034 and 2,004,048); polyisocyanates containing urethane groups (Belgian Pat. No. 752,261 or U.S. Pat. Nos. 3,394,164 and 3,644,457); polyisocyanates containing acylated urea groups (German Pat. No. 1,230,778); polyisocyanates containing biuret groups (U.S. Pat. Nos. 3,124,605; 3,201,372; and 3,124,605 and British Pat. No. 889,050); polyisocyanates produced by telomerization reactions (U.S. Pat. No. 3,654,106); polyisocyanates containing ester groups (British Pat. Nos. 965,474 and 1,072,956, U.S. Pat. No. 3,567,763 and German Pat. No. 1,231,688); reaction products of the above-mentioned isocyanates with acetals (German Pat. No. 1,072,385); and polyisocyanates containing polymeric fatty acid esters (U.S. Pat. No. 3,455,883).

It is also possible to use the isocyanate-containing distillation residues obtained in the commercial production of isocyanates, optionally in solution in one or more of the above-mentioned polyisocyanates. It is also possible to use mixtures of the above-mentioned polyisocyanates.

In general, it is particularly preferred to use the commercially readily available polyisocyanates. Examples include 2,4- and 2,6-tolylene diisocyanate; also mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates"); particularly modified polyisocyanates of the type derived from 2,4- and/or 2,6-tolylene diisocyanates or from 4,4'- and/or 2,4'-diphenyl methane diisocyanate.

According to the present invention, component (B) may also comprise NCO-groups containing reaction products of the above-mentioned polyisocyanates and the high molecular weight and/or low molecular weight polyhydroxyl compounds known from polyurethane chemistry (so-called "NCO-prepolymers"). Monoisocyanates, such as methyl, benzyl, phenyl or tolyl isocyanates, are also suitable for the process according to the present invention.

For denaturing biomasses in accordance with the present invention, it is of particular economic advantage to use the distillation residues accumulating in the commercial production of isocyanates for which it has not yet been possible to find practical use, as explained above in connection with the biomasses, and whose elimination has hitherto also involved considerable problems (cf. in this connection, for example, German Offenlegungsschriften Nos. 2,846,815 and 2,846,809 and U.S. patent application Ser. Nos. 88,800 and 89,322). Distillation residues particularly suitable for the purposes of the present invention are the substantially monomer-free, cross-linked distillation residues which are insoluble in inert organic solvents and which cannot be melted without decomposing. These are of the type which accumulate as slag in the removal of monomeric tolylene diisocyanates by distillation from crude phosgenation products of tolylene diamines, optionally after stirring into water, and which before use are ground into a powder and, optionally, chemically modified simultaneously and/or subsequently by reaction with compounds reactive with the functional groups of the distillation residue, particularly the isocyanate groups.

As mentioned above, the distillation residues used in the process according to the present invention automatically accumulate in the conventional process for the production of 2,4- and/or 2,6-tolylene diisocyanate on an industrial scale. They are in the form of relatively high molecular weight residue slags cross-linked by way of main valency bonds which are generally formed in a quantity of more than 10%, by weight, based on the calculated quantitative yield of monomeric diisocyanates. To make them easier to handle they are generally introduced into water at a temperature above 150° C., resulting in the formation of a coarse-grained, irregularly shaped insoluble slag in which a large number of the free isocyanate groups have reacted to form polyurea groups. Although this slag still has a small content of free NCO-groups (generally less than 15%, by weight and, in most cases, from 1 to 10%, by weight), it is substantially free from monomeric diisocyanates. In addition to the NCO-groups, the TDI residue slags contain urea, biuret, uretdione isocyanurate, carbodiimide, uretone imine and, in some cases, even methyl benzimidazolone groups and the biuretization products thereof in varying quantitative ratios. The slags are so highly cross-linked by way of these various functional groups that, even after size-reduction to a mean particle size of less than 5 μm, they are substantially insoluble in inert organic solvents, such as methylene chloride, cyclohexane, cyclohexanone, toluene, xylene or dichlorobenzene, even at boiling temperature. Even in boiling dimethyl formamide, the residue powders are only partly swollen, but not dissolved. On heating, only a very small proportion, if any, of the TDI distillation residues used in accordance with the present invention softens at temperatures above about 250° C., although beyond about 280° C. the distillation residues decompose without melting, giving off gases in the process.

Some of the above-mentioned groups in the TDI slag, for example, uretdione and carbodiimide groups, may additionally react chemically with the biomasses at elevated temperatures.

The very coarse-grained TDI residue slag is preferably first pre-comminuted to less than 3 mm in a comminuting machine, for example, a cutting granulator or a hammer mill, and is then brought to the final particle size required at any stage using known wet or dry grinding processes.

In cases where the TDI residues accumulate in water or are wetted with water, it is particularly economical or environmentally desirable to subject the coarse TDI slag to wet grinding in the aqueous biomass suspension in batch-type or continuous machines optionally arranged one behind the other in two stages. The solids content of these mixtures during grinding preferably amounts to from 10 to 45%, by weight. Depending on the required grain size, the wet grinding may be done in tube and ball mills, toothed colloid mills, trigonal gear ring mills, corundum disc mills and stirrer-equipped ball mills.

In certain cases, some or all of the water may be replaced during grinding by another liquid.

The TDI residue slags obtained after wet grinding which contain different quantities of free NCO-groups, depending on the procedure adopted, are used either in the form of very finely divided suspensions or pastes or (after isolation of the suspending agent) in the form of powders in the same way as the TDI residue powders obtainable by dry grinding.

TDI residue slags which have been pre-ground to less than from 2 to 3 mm and pre-dried, preferably at temperatures below 50° C., and which have a moisture content of not much more than 20%, by weight, and preferably less than 10%, by weight, are used for dry grinding. The choice of the particular machines used for dry grinding is essentially governed by the final particle size and particle size distribution required and by the grinding costs. In comparison with plastics, the residue slags used in accordance with the present invention are very hard. By virtue of the high degree of cross-linking, they may be ground without softening at temperatures up to about 200° to 300° C. in conventional size-reducing machines free from cooling problems, which is of particular importance for obtaining very fine particle sizes.

Grinding may be carried out, for example, in pinned-disc mills, ball mills, baffle plate mills, air-stream mills, cross-beater mills, gear ring mills or turbine mills. It is preferred to use steam-jet or air-jet mills because, in mills of this type, size-reduction is primarily obtained by inter-particle collisions and secondarily by wall collisions. Very fine particle sizes may thus be obtained in a single passage.

Dry grinding may also be carried out by single-stage and multi-stage, batch-type or continuous grinding processes.

As a result of wet or dry grinding, the residual reactive groups of the above-mentioned type which are included in the residue slag are made available for a variety of chemical reactions with the biomasses.

The residue powder should have a particle size of less than 2 mm preferably less than 0.8 mm, more preferably less than 0.4 mm and, with particular preference, less than 0.1 mm, to enable the polyaddition reactions with the biomasses to take place substantially quantitatively.

Further particulars on the production of the TDI residue powders used in the process according to the present invention may be found in German Offenlegungsschrift No. 2,846,815 and U.S. Pat. No. 4,297,456. The earlier disclosure also contains a detailed description of possible modification reactions on the TDI residue powders (for example by means of carbonyl compounds or compounds containing Zerewitinoff-active hydrogen atoms) which may optionally be carried out before the powders are used in accordance with the present invention.

The present process may be carried out in various ways, depending on whether dried biomasses or biomasses dispersed in water are used as the starting material. Where the process is carried out in the aqueous phase, biomasses having a solids content of from 0.3 to 20%, by weight, preferably from 1 to 15%, by weight, are generally used. The aqueous surplus activated sludges from biological purification plants generally have a solids content of from 0.3 to 3%, by weight, more particularly from 0.7 to 1.5%, by weight. The quantity in which the isocyanate is used where the process is carried out in the aqueous phase amounts to from about 2 to 95%, by weight, preferably from 3 to 80%, by weight, (based on the sum of the dry weight of the biomass and the weight of the isocyanate) and is also governed by the type of isocyanate used. Low molecular weight monoisocyanates and polyisocyanates (molecular weight up to about 500), of the type described in detail above, are preferably used in quantities of from 3 to 20%, by weight, while relatively high molecular weight polyisocyanates (including in particular the TDI residue powders) are preferably used in quantities of from about 20 to 80%, by weight, (based in each case on the sum of the isocyanate and the dry weight of the biomasses). If the isocyanate is present in a stoichiometric excess in relation to the H-acid groups of the biomass, biomass-isocyanate polyadditon products containing free NCO groups, which may be of particular advantage for some applications of the products (for example as reactive fillers), are obtained in accordance with the present invention.

In cases where isocyanates which are liquid under the reaction conditions or which are dissolved in an organic solvent are used, the denaturing reaction is preferably carried out at temperatures of from 50° to 200° C. and, with particular preference, from 80° to 120° C. Denaturing using the above-described TDI residue powders generally required somewhat higher temperatures, for example from 70° to 200° C., and preferably from 90° to 150° C. In cases where a solvent is used, the reaction temperature may generally be reduced by about 20° to 30° C. in relation to the solvent-free procedure.

In cases where biomasses dispersed in water are used as the starting material in accordance with the present invention it is advantageous, particularly if the starting material is relatively coarse, to also use an organic solvent in a quantity of from 1 to 30%, by weight, preferably from 5 to 10%, by weight, based on the dispersion, in order to facilitate the reaction between the generally hydrophobic isocyanates and the aqueous biomass. The organic solvent used is preferably at least partly miscible with water. Solvents suitable for use in the process according to the present invention, which may also contain isocyanate-reactive groups, are for example, acetone, methyl ethyl acetate and mixtures thereof.

Where the process is carried out in the aqueous phase, it is preferred to apply temperatures of from 80° to 130° C. Pressure may also be applied, for example, an excess pressure of from 2 to 100 bars. The pH value is generally from 1 to 10, preferably from 4 to 8. If necessary, the pH may be adjusted to the required range by the addition of acids or alkali or ammonia. The application of high temperatures and low pH values during the isocyanate polyaddition reaction promotes plasmolysis, i.e. shrinkage of the protoplasma, and partial hydrolysis of the cell material.

The polyaddition reaction in the aqueous phase may be carried out both in batches in conventional reaction vessels and also (optionally in combination therewith) continuously. Straight-flow mixers, of the type described, for example in German Patent No. 2,513,815 (U.S. Pat. No. 4,089,835), or multiphase reaction tubes according to German Offenlegungsschrift No. 2,719,970 (U.S. Pat. No. 4,119,613) and the apparatuses described in the literature cited therein may be used. In the continuous processes, the average residence time of the reaction mixture of concentrated aqueous biomass, isocyanate and, optionally, solvent preferably amounts to from between about 2 to 20 minutes and, with particular preference, from 1 to 5 minutes for temperatures near the boiling point. It is of particular advantage to use a multiphase flow-type reaction tube because substantially quantitative drying of the polyaddition product is also obtained in this way. Where the polyaddition reaction according to the present invention is carried out in batches in conventional reaction vessels, the surplus activated sludge from biological purification plants is denatured and flocculated by the polyaddition reaction to such an extent that the process products may be isolated by filtration resulting in a solids content of more than 50%, by weight, (even without the otherwise necessary filtration aids).

In cases where substantially anhydrous powders of biomasses are used for the process according to the present invention, it may be assumed that the cells have died, leaving only a small residue of living cells. As mentioned above, however, an activated sludge powder, for example, is still attended by an intolerable odor. In the same way as the latent residual activity, this odor may be completely eliminated by the isocyanate polyaddition reaction of the present invention. To this end, the powder-form biomass may be intensively mixed with a large excess (of NCO groups) of a liquid or dissolved monoisocyanate or polyisocyanate. The addition reaction takes place at temperatures as low as room temperature, albeit over a period of a few days. It is preferable to briefly heat the mixture (preferably for from 3 minutes to 3 hours, depending on the temperature) to a temperature of from about 50° to 200° C., preferably from 80° to 150° C., and, after reaching a constant NCO content, to remove the excess, unused low molecular weight isocyanate, optionally by means of a solvent, such as acetone. A powder-form insoluble biomass polyisocyanate having an NCO content which may amount to more than 15%, by weight, is obtained. The reaction of the dry biomass with an equivalent or subequivalent quantity of isocyanates leads to NCO-free sterilized biomass polyaddition products. In this embodiment of the process, too, the isocyanate is used in a quantity of from 2 to 95%, by weight, preferably from 3 to 80%, by weight, (based on the total quantity of biomass and isocyanate). The reaction may be carried out either as such or in the above-mentioned organic solvents (in which case the solvent is used in a quantity of from 1 to 50%, by weight, preferably from 5 to 20%, by weight, based on the reaction mixture). Where substantially anhydrous biomasses and a liquid organic solvent are used, the process may again be carried out in batches in conventional reaction vessels and also continuously in straight-flow mixers, multiphase reaction tubes or in reaction screw extruders.

It is of particular technical significance, above all when, in addition to the biomasses, the reaction mixture contains only small quantities of liquid components (for example solvents or liquid reactants for the biomasses) and when the powder-form TDI residues slags described in detail above are used as the isocyanate component, to apply two processes which may optionally be coupled with one another. For the first process, the known centrifuging and fluidizing technique carried out by means of mechanically active mixers or mixing tools and/or for the second, the fluidized-bed technique. For the first technique, it is best to use commercially available heatable and coolable mixers in which plowshare-like blades arranged on a rotatable shaft and, optionally, independently movable cutter heads are mounted in the mixing drum.

Providing the process conditions under which a substantially powder-like form is maintained during the polyaddition reaction according to the present invention (temperature; residence time) are determined first by laboratory tests and then by semi-technical tests in from 100 to 200 liter mixers, it is possible without major difficulties to use large-capacity mixing units optionally arranged one behind the other for producing commercial quantities of biomass isocyanate polyaddition products.

For applying the second technique, namely the fluidized bed technique, the optimal state of fluidization in the fluidized bed is difficult to calculate and, for given solids data, such as density, particle sizes and distribution, and the selected flow medium (for example air or nitrogen), is essentially determined by the difference between the loosening rate and the rate of flow of the flow medium. The optimal state of fluidization may readily be determined by a few preliminary tests carried out in a small laboratory fluidized bed. The optional use of liquid or gaseous reaction components should be taken into account in these preliminary tests.

In cases where the fluidity of a packing proves to be inadequate during the process (i.e. where a certain tackiness occurs), it is possible in certain cases to use a granular material of higher specific gravity (for example quartz sand) and to isolate the polyadduct in a cyclone.

In fluidized beds characterized by high through-flow rates, fine size-reduction may be obtained by vigorous agitation of the solids, possibly even during the reactions according to the present invention.

As mentioned above, it is also possible in one particular embodiment of the present invention to carry out condensation reactions with carbonyl compounds and, optionally, compounds suitable for aminoplast and/or phenoplast formation in the biomasses before, after or during the isocyanate polyaddition reaction according to the present invention. Such condensation reactions are only the subject of the present invention insofar as they are used in combination with isocyanate polyaddition reactions in the manner described above.

The simplest modification is to allow formaldehyde to act on the biomasses. Depending on the pH value, the biomasses initially only undergo methylolation or cross-linking reaction (preferably in the strongly acid range) which results in the formation of methylene bridges. In addition to a carbonyl compound suitable for condensation with the biomasses, it is also possible, as mentioned above, to add other compounds capable of condensation. In addition, however, compounds capable of condensing with carbonyl compounds are also formed during the isocyanate polyaddition reaction itself. It is of particular advantage to add urea or to form urea groups capable of condensation and also to use azulmic acid (cf. for example the summary by Th. Volker in Angewandte Chemie 1960, pages 379-384) which, as a polymeric hydrocyanic acid, contains numerous amino groups. In addition, azulmic acid, which is also reactive to isocyanates, is also capable of complexing heavy metal ions. Accordingly, biomass azulmic acid polyisocyanate polyaddition products modified in accordance with the present invention are particularly suitable for use as plant nutrients. In addition, they considerably increase the nitrogen content of the products.

Suitable carbonyl compounds, which may optionally be used as reaction components for carrying out the process according to the present invention, are any of the conventional carbonyl compounds containing sufficiently reactive carbonyl groups. Preferred carbonyl compounds are aldehydes and ketones.

Particularly preferred aldehydes are saturated, aliphatic (optionally halogen- or hydroxy-substituted monoaldehydes), such as formaldehyde, acetaldehyde, butyraldehyde, isobutyraldehyde, pivalic aldehyde, chloral, hydroxy acetaldehyde, hydroxy pivalic aldehyde, glyceric aldehyde, hydroxy aldehydes of the type present in formose-sugar mixtures and hydroxy aldehydes formed from other aldehydes by aldol condensation reactions. Other particularly preferred aldehydes are unsaturated aliphatic aldehydes (such as acrolein and crotonaldehyde), cycloaliphatic aldehydes (such as cyclohexane aldehyde, aliphatic dialdehydes, such as glyoxal, methyl glyoxal, glyoxal sulfate and glutaric dialdehydes), aromatic aldehydes (such as benzaldehyde, 4-methyl benzaldehyde, salicylic aldehyde and terephthalic dialdehyde), and aldehydes derived from heterocycles (such as furfurol and hydroxy methyl furfurol). It is also possible with advantage to use "masked aldehydes", i.e. compounds which either release aldehydes or react like aldehydes under the reaction conditions. In this connection, particular reference is made to paraformaldehyde, trioxane, chloral hydrate, hexamethylene tetramine and semi-acetals of aldehydes, in particular formaldehyde with monofunctional, difunctional or higher polyfunctional alcohols, such as methanol, ethanol, butanol, ethylene glycol and diethylene glycol.

Particularly preferred ketones are hydroxy acetone, dihydroxy acetone, methyl ethyl ketone, methyl isobutyl ketone, cyclohexanone and acetophenone and quinones, such as benzoquinone.

It is also possible to use mixtures of aldehydes and/or ketones. Mixtures of formaldehyde and other aldehydes or ketones are particularly preferred. Hydroxy aldehydes and hydroxy ketones may be formed in situ by aldol condensation reactions from mixtures such as those of formaldehyde with aldehydes or ketones containing hydrogen atoms in the α-position. The hydroxy aldehydes and polyhydroxy ketones readily enter into addition reactions with, for example, urea and numerous aminoplast formers during formation thereof, particularly in the mildly to strongly alkaline range, to form N-alkylol compounds which in turn represent condensation partners for the above-mentioned biomasses.

Suitable thiocarbonyl compounds, which may be used as reaction compounds for carrying out the process according to the present invention, are conventional thiocarbonyl compounds containing sufficiently reactive thiocarbonyl groups. Preferred such thiocarbonyl compounds are thioaldehydes and thioketones. Particularly preferred thioaldehydes and thioketones are those derived from the aldehydes and ketones which are mentioned above as being particularly preferred.

It is also advantageous to use "masked thioaldehydes", i.e. compounds which release thioaldehydes under the reaction conditions. Reference is made in particular to trimeric thioformaldehyde (trithian) which decomposes into thioformaldehyde at elevated temperatures in the presence of acids.

Carbonyl compounds which are in dissociation equilibrium with low molecular weight uncondensed N-alkylol compounds are, preferably, simple aldehydes, particularly formaldehyde, which is in equilibrium with the corresponding N-methylol compounds. Such N-methylol compounds include, in particular, N-methylol urea, N,N'-dimethylol urea, methylolated dicyanodiamide, methylolated oxamide, N-methylol thiourea, N,N'-dimethylol thiourea and methylolated melamines. Examples of methylolated melamines include hexamethylol melamine and tris-hydroxy methyl melamine corresponding to the following formula:

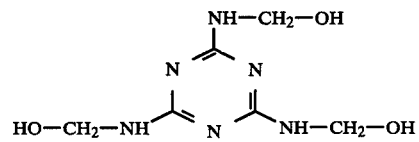

Reference is also made to monomethylol ethylene urea corresponding to the following formula:

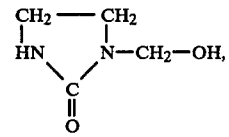

to monomethylol ethylene thiourea corresponding to the following formula:

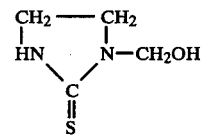

and to tetramethylol acetylene diurea corresponding to the following formula:

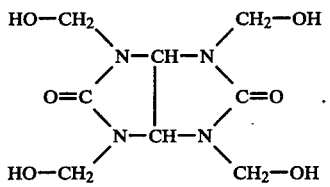

It is also possible to use alkylol compounds of the type derived from simple aldehydes, preferably those containing up to 5 carbon atoms.

The following compounds are used with particular preference as carbonyl compounds for carrying out the process according to the present invention: formaldehyde, acetaldehyde, isobutryaldehyde, crotonaldehyde, glyoxal, furfurol, hydroxy methyl furfurol, salicylic aldehyde and semi-acetals thereof. Polymers of formaldehyde (such as paraformaldehyde and trioxane) hexamethylene tetramine and thioaldehydes (such as thioformaldehyde) may also be used. The uncondensed (low molecular weight) N-alkylol compounds preferred for use in the present invention are N-methylol urea, dimethylol urea, trimethylol melamine, hexamethylol melamine, monomethylol ethylene urea, monomethylol ethylene thiourea and tetramethylol acetylene diurea.

As mentioned above, aminoplast formers may also be used in the process according to the present invention for modifying the biomasses. In the context of the present invention, aminoplast formers are understood to be nitrogen compounds which are capable of forming N-oligocondensation and N-polycondensation products with reactive carbonyl compounds.

Aminoplast formers which correspond to this definition are nitrogen compounds. Examples includeureas (for example urea itself, acetylene urea, dimethyl acetylene urea and N-methylene urea), thioureas (such as unsubstituted thiourea), diureas (such as hexamethylene diurea, tetramethylene diurea and ethylene diurea), polyureas (such as the type obtained by reacting aliphatic, cycloaliphatic or araliphatic diisocyanates, triisocyanates or biuret-polyisocyanates with ammonia, primary amines, or polycarboxylic acid amines, such as oxalic acid diamide, succinic acid diamide and adipic acid diamide), monourethanes, diurethanes and higher polyurethanes (such as the reaction products of aliphatic, cycloaliphatic, araliphatic and aromatic mono- or bis-chloroformic acid esters with ammonia or primary amines), biurets, melamines (such as melamine itself), amidines (such as dicyanodiamidine), guanidines (such as aminoguanidine), guanazoles, guanamines, cyanamide, dicyanodiamide, primary monoamines, secondary monoamines, arylamines, ammonia, diamines, triamines, hydrazines and carboxylic acid hydrazines (such as hydrazodicarbon amide, carbazinic acid esters and hydrazodicarboxylic acid esters), also similar nitrogen compounds capable of aminoplast formation, preferably the derivatives containing N-alkylol groups, preferably N-methylol groups, corresponding to the above-mentioned nitrogen compounds and the corresponding $C_1$–$C_4$ alkyl ethers of these N-alkylol derivatives may be used.

Other preferred aminoplast formers are $\alpha,\omega$-diureas of relatively high molecular weight, N-methylol derivatives thereof and N-methylol alkyl ethers. $\alpha,\omega$-bis-alkoxy methyl urethanes containing polyether, polythioether, polyacetal, polyester amide or polycarbonate residues having an average molecular weight of from 400 to 10,000 and, optionally, additional urethane or substituted urea groups between the functional groups in the $\alpha,\omega$-position are also preferred. In this respect, particularly preferred relatively high molecular weight nitrogen compounds capable of aminoplast formation are compounds which may be dissolved or dispersed in water. Examples include compounds which, between the functional urethane or urea groups in the $\alpha,\omega$-position, contain polyethylene oxide residues or residues of copolymers of ethylene oxide with propylene oxide or tetrahydrofuran or of water-soluble polyacetals produced from di-, tri- or tetraethylene glycol and formaldehyde.

These aminoplast formers suitable for use as starting compounds are known or may be produced by methods known in principle (cf. Houben-Weyl "Methoden der Organischen Chemie", Vol. XIV, Part 2 (1963), pages 319–402, Georg Thieme-Verlag, Stuttgart).

"Modified aminoplast formers" may also be used as aminoplast formers in the process according to the present invention. Modified aminoplast formers are aminoplast formers which contain additional groups readily capable of incorporation. Examples of modified aminoplast formers are compounds which may be rapidly and easily incorporated by mixed condensation. Such compounds are preferably polyurethanes and polyureas containing terminal $NH_2$ groups, polyamides of poly-($\beta$-alanine) having molecular weights of up to 2000, N-methylol methyl ethers of polycaprolactam, polythiolactams, polypeptides of N-carboxy-$\alpha$-aminocarboxylic acids, low molecular weight polyamides of aliphatic dicarboxylic acids and diamines, polyamides of cycloaliphatic components and aromatic components, polyamides containing O- and S- or N- as heteroatoms, and polyester amides. Mixed condensates which, in addition to amide groups, also contain ester, urethane or urea groups; ethoxylated and propoxylated monoamides and polyamides; polyhydrazides; polyaminotriazoles; polysulfonamides; formaldehyde mixed condensates with urea, melamine and dicyanodiamide; low molecular weight aniline formaldehyde condensates; sulfonic acid amides; mononitriles and dinitriles; acrylonitrile; urotropin; hexahydrotriazines of primary amines and formaldehyde; Schiff's bases and ketimines or polyketimines, for example those from 1 mole of hexamethylene diamine and 2 moles of cyclohexanone; polyaddition products and polycondensation products of melamine and other aminoheterocycles with aldehydes and alcohols; polyaddition and polycondensation products of nitriles with aldehydes; reaction products of phosphorous acid and dialkyl phosphates with carbonyl compounds and amines or polyamines may also be used. In this connection, other suitable compounds capable of aminoplast formation are the compounds which are described on pages 7 to 12 of German Offenlegungsschrift No. 2,324,134.

Other modified aminoplast formers which may be used in the process according to the present invention are N-alkylol compounds and, in particular, N-methylol compounds which are partly etherified with polyhydroxyl compounds.

The proportion of alcohols or polyhydricalcohols in these products may amount, depending on the component, to 60%, by weight, based on the sum of the percentages of nitrogen compounds and alcohols.

The following compounds inter alia are particularly suitable for use as aminoplast formers in the process according to the present invention: urea, thiourea, diureas, such as hexamethylene diurea, tetramethylene diurea, ethylene urea, acetylene urea, dimethyl acetylene urea, oxalic acid diamide, succinic acid diamide, adipic acid diamide, mono- or bis-hydrazines (such as hydrazodicarbonamide, carbazinic acid methyl and ethyl esters), hydrazodicarboxylic acid esters, monourethanes and, in particular, diurethanes (such as the reaction products of aliphatic, cycloaliphatic, araliphatic and aromatic mono- or bis-chloroformic acid esters with ammonia and primary amines), aniline melamine, dicyanodiamide, cyanamide, aminoguanidine, dicyanodiamidine, guanamines, guanazoles, polyureas and polybiurets (particularly the type obtained by reacting aliphatic, cycloaliphatic, araliphatic diisocyanates or triisocyanates) and biuret polyisocyanates with an excess of ammonia or primary amines.

Other aminoplast formers which may be used in the process according to the present invention are substantially defect-free azulmic acids, defect-containing so-called "modified azulmic acids", azulmic acids stabilized by condensation with carbonyl compounds, azulmic acids stabilized by condensation with carbonyl compounds and aminoplast formers or low molecular weight condensation products thereof and also metal salt complexes of the above-mentioned azulmic acids. These compounds are preferably used together with other aminoplast formers, particularly urea, in the process according to the present invention.

These various azulmic acids are known and are described in detail in Houben-Weyl, Methoden der Organ. Chemie (1952), Vol. 8, page 261; in Angewandte Chemie 72, (1960), pages 379-384; in German Pat. Nos. 662,338 and 949,600 and in German Offenlegungsschriften Nos. 2,806,019 and 2,806,020 and U.S. patent application Ser. Nos. 11,554; 84,002; and 82,839 and U.S. Pat. No. 4,252,919.

Phenoplast formers suitable for use in the process according to the present invention are the known phenols and derivatives thereof, such as phenol, cresol, bisphenol A, nitrophenol, pyrocatechol, hydroquinone and naphthol sulfonic acid. Other aminoplast and phenoplast monomers suitable for use as modifying agents are described in German Offenlegungsschriften Nos. 2,324,134; 2,713,198 and 2,738,532.

In addition, biomasses which have been denatured by the process according to U.S. patent application Ser. No. 84,002, now abandoned may also be used in the process according to the present invention. Such biomasses are obtained by condensing them in aqueous medium with carbonyl compounds, thiocarbonyl compounds and/or carbonyl compounds which are in dissociation equilibrium with low molecular weight, uncondensed N-alkylol compounds, optionally in the presence of a catalyst and optionally in the presence of additives, in a first reaction phase, optionally with hydrolytic degradation or denaturing of the cell walls present in the biomasses. The unreacted carbonyl compounds, thiocarbonyl compounds and/or carbonyl compounds which are in equilibrium are reacted with low molecular weight, uncondensed N-alkylol compounds with aminoplast formers optionally containing N-alkylol groups or with phenoplast formers in a second reaction phase carried out in aqueous medium optionally in the presence of a catalyst, optionally in the presence of chain-terminators and optionally in the presence of additives. The thus-obtained modified biomasses may optionally be freed from undesirable substances still present and/or subjected to an after-treatment.

The polyaddition products of denatured biomasses, isocyanates and, optionally, aminoplast or phenoplast formers produced in accordance with the present invention may be after-treated by treating them with a variety of reagents at temperatures of from 0° to 200° C., preferably from 10° to 140° C. and, with particular preference, from 30° to 120° C., optionally in the presence of diluents, such as anhydrous organic solvents. In this way, chemical reactions take place essentially on the surface of the products so that chemically surface-modified products are obtained.

This chemical surface modification of the polyaddition products obtainable by the process according to the present invention is preferably obtained by treatment with urea melts; treatment with acylating agents, such as formic acid, acetic acid anhydride or mixed acid anhydrides of acetic acid and oleic acid (preferably in the presence of sodium or potassium acetate); cyclic acid anhydrides, such as maleic acid anhydride, phthalic acid anhydride or hexahydrophthalic acid anhydride; melts of dicarboxylic acids, such as adipic acid, phthalic acid, hexahydrophthalic acid or trimellitic acid; inorganic acid chlorides, such as cyanogen chloride, phosgene, thionyl chloride, sulfur chlorides, phosphorus oxychloride, phosphorous pentachloride, silicon tetrachloride, antimony trichloride or titanium tetrachloride; inorganic acid chlorides, such as acetyl chloride, benzoyl chloride, chloroformic acid esters, benzene sulfonic acid chlorides, phosphoric acid ester chlorides, chloromethane sulfochloride or cyanuric acid chloride; treatment with alkylating agents, such as dimethyl sulfate, methyl iodide or methyl bromide, dichloroethane, glycol chlorohydrin, chloroacetic acid ethyl ester, dichloroacetic acid ethyl ester, chloroacetaldehyde diethyl acetal, allyl chloride, benzyl chloride, trichloromethyl isocyanide dichloride or other isocyanide dichlorides; treatment with ε-caprolactam, ε-caprolactone, hydroxy pivalic acid lactone, cyclic 6-membered or 8-membered siloxanes, azalactams of the type known from German Offenlegungsschrift No. 2,035,800, glycol carbonate, ethylene oxide, propylene oxide, butylene oxide, styrene oxide, epichlorohydrin, butyrolactone, valerolactone, oxazolidines, oxazolines, imidazolidines, isatoic acid anhydride or Leuch's anhydrides of aminoacids and phosgene; treatment with acrylonitrile or other vinyl monomers, such as acrylic acid, methacrylic acid or methyl, ethyl, β-hydroxy ethyl or propyl esters thereof; treatment with hydroxy alkane phosphonic acid esters or the parent acids, particularly with hydroxy methyl phosphonic acid esters or with the free hydroxy methyl phosphonic acid; treatment with chloromethyl alkoxy silanes; treatment with a variety of mononitriles or polynitriles, preferably hydroxy methyl nitrile, under the conditions of Thorpe's reaction catalyzed by hydroxy anions; treatment with polyisocyanates of the above-mentioned type in the presence of isocyanate-reactive compounds known from polyurethane chemistry (particularly polyols having a molecular weight of from 62 to 500). In this way, the denatured biomass may be surrounded by a polyurethane shell without the material losing its powder-form consistency. A similar effect is obtained by after-treating the above-mentioned denatured biomass still containing free NCO-groups with polyols or by subjecting them to carbodiimide formation.

Other suitable after-treatment reagents include sodium hydroxide, potassium hydroxide, calcium hydroxide, sodium sulfide, rongalite ammonium polysulfides, diethyl phosphite and dimethyl phosphite.

During these after-treatment reactions, it is also possible to carry out a variety of copolymerization or polymerization reactions involving vinyl monomers. In this case, the biomass mixed condensates are surrounded or microencapsulated by the polymers formed. The "shell materials" may, of course, also be used in a large excess.

In the same way as the polyurethane-coated products mentioned above, biomasses modified in this way may be directly molded under heat (i.e. without the addition of further binders) to form shaped articles.

In certain cases, the modification reactions on the biomasses discussed above under the generic heading of "after-treatment" may even be carried out before or at the same time as the polyaddition reaction according to the present invention. It is also possible, after the polyaddition reaction, to produce from the products, polymethylene ureas, polyalkylidene ureas and other substantially insoluble or completely insoluble compounds, for example highly cross-linked aminoplast condensates which, on account of their insolubility, show virtually no covalent bonds to the biomass. Such mixtures, in which the quantity of the non-covalently bound fraction of aminoplast condensates or phenoplast condensates may be varied as required, represent extremely interesting flameproofing agents for a variety of plastics, particularly where they are charged with polymethylene thioureas, cross-linked polymethylene melamine powders, urea hydrazodicarbonamide formaldehyde condensates and dicyanodiamide or oxamide condensates.

It is also advantageous to subsequently charge the products with substantially insoluble melamine phosphate, substantially insoluble urea oxalate, urea nitrate or substantially insoluble ammonium magnesium phosphate. The addition of alumina hydrates, aluminum oxides, alumosilicates, calcium carbonate, quartz powder and the addition of linear or cross-linked polymethylene ureas, powdered melamine formaldehyde condensates, urea hydrazodicarbonamide condensates and high molecular weight polyammonium polyphosphates are also of importance. The products obtained in this case are eminently suitable for use as flameproofing agents for plastics.

In addition, other additives which may advantageously be used in the process according to the present invention, particularly in cases where azulmic acids are used, are sugars, such as cane sugar and other sugars which do not contain free aldehyde groups or even formose-sugar mixtures produced from formaldehyde. These various types of sugars may be fixed in passages and pores of the azulmic acid. In addition, the various sugars may even be attached to the mixed condensates in the form of the generally substantially insoluble calcium complexes thereof.

In addition, it is always possible when the polyadducts according to the present invention contain azulmic acids to simultaneously gas the products with ammonia and carbon dioxide after production. In this case, the small molecules of ammonia and carbon dioxide penetrate into the azulmic acid skeleton to a considerable extent.

In addition to the reactive aminoplast, phenoplast and vinyl monomers and other reactive low molecular weight compounds which have been described in detail, it is possible to add to the biomasses in the process according to the present invention a variety of different fillers and additives. Examples include organic naturally occurring substances and products obtained therefrom, inorganic naturally occurring substances and products obtained therefrom, synthetic organic products, synthetic inorganic products and/or mixed organic/inorganic products.

Preferred organic natural substances and products obtained therefrom are wood powder or chips, lignin powder, lignin sulfonic acids, ammoniated lignin sulfonic acids, humus, huminic acids, ammoniated huminic acids, peat, proteins and the degradation products thereof. Other examples include polypeptides, wool, gelatin, fish meal, bone meal, pectins, polysaccharides (such as starch and cellulose), hemicelluloses, homogenized materials of vegetable and animal origin, active carbon and ashes obtained by the incineration of organic substances formed by photosynthesis or conventional fuels.

Preferred inorganic natural substances and products obtained therefrom are silicates (such as aluminum silicates, calcium silicates, magnesium silicates and alkali silicates), silicas (particularly disperse silicas and silica gels), clay minerals, mica, carbonates (such as calcium carbonate), phosphorite and phosphates (such as calcium phosphate and ammonium magnesium phosphate), and sulfates (such as calcium sulfate).

In addition to natural or synthetic rubbers, polyamides and epoxide resins, preferred synthetic organic products are the aminoplast and phenoplast resins described in detail above.

Other particularly suitable additives are powder-form TDI residue slags of the type described above, the NCO groups of which have been quantitatively removed by reaction with water or other H-acid compounds (TDI distillation residues modified in this way are also described in the above-mentioned German Offenlegungsschriften Nos. 2.846,809 and 2,846,815 and U.S. Pat. Nos. 4,251,638 and 4,297,456. Even if they are free from NCO groups, such powders still contain numerous reactive groups (for example urea, urethane, carbodiimide and/or uretdione groups) which may participate in the polyaddition and polycondensation reactions taking place in the process according to the present invention.

Preferred synthetic inorganic products are fertilizers (such as super phosphate, Thomas slag, rhenania phosphate, phosphorite, calcium cyanamide, calcium ammonium nitrate, Leuna saltpeter, potassium phosphates, potassium nitrate and ammonium nitrate), pigments (such as iron oxides and titanium dioxides), and in particular the inorganic primary sludges from biological purification plants.

The polyaddition products of denatured biomasses, isocyanates and, optionally, additives produced in accordance with the present invention are eminently suitable for use as agrochemicals, particularly when they do not contain free NCO groups. Agrochemicals are chemicals which may be used for a variety of purposes in agriculture and gardening.

Thus, the substances produced in accordance with the present invention may be used, for example, as fertilizers both for supplying plants with macronutrients and also for supplying plants with micronutrients. They are particularly suitable for use as long-term nitrogen fertilizers. Of particular interest in this respect are those substances usable in accordance with the present invention which contain ions required by plants, such as ammonium ions, lithium, sodium, potassium, beryllium, magnesium, calcium, strontium, barium, aluminum, zinc, manganese, nickel, cobalt and iron ions.

Those substances usable in accordance with the present invention which contain anions, such as chloride, nitrate, sulfate and/or phosphate, are also of particular interest as fertilizers.

Those substances according to the present invention which contain several of the above-mentioned types of ions alongside one another are particularly preferred as fertilizers. Such substances, are for example, substances which contain both potassium and/or ammonium ions and also nitrate and/or phosphate ions.

In addition, those substances according to the present invention which, optionally in addition to nutrient ions, contain the organic additives described in detail above are of particular interest as fertilizers.

The substances of the present invention, optionally in addition to containing nutrient ions, may be used in combination with commercial fertilizers may be used as fertilizers. Particularly suitable commercial fertilizers are super phosphate, Thomas slag, rhenania phosphate, phosphorite, calcium cyanamide, calcium ammonium nitrate, Leuna saltpeter, potassium phosphates, potassium nitrate and ammonium nitrate, urea formaldehyde condensates, urea crotonaldehyde condensates, urea isobutyraldehyde condensates and condensates of dicyanodiamide, melamine or octamide with aldehydes (such as formaldehyde, acetaldehyde, crotonaldehyde or isobutyraldehyde) are also suitable.

Those substances according to the present invention which, optionally in addition to nutrients, also contain biologically active garden soil may also be used as fertilizers.

In cases where compounds according to the present invention produced from biomasses containing heavy metal salts are used as fertilizers, it is necessary to add azulmic acids, thiourea or other compounds having a strong complexing action as aminoplast formers during the production of these products. In this way, heavy metal ions present in the biomasses (for example, ions of lead, copper, mercury, cadmium or zinc) are bound so firmly that no plant damage occurs.

Particularly preferred fertilizers are products based on biomasses free from heavy metals of the type which accumulate, for example, in fermentation processes in the pharmaceutical, enzyme, food and luxury food industries. Also biomasses free form heavy metals emanating from biological or fully biological purification plants for industrial and communal effluents are particularly preferred.

Biomass mixed condensates according to the present invention which, by the use of isobutyraldehyde, also contain segments corresponding to the following structure:

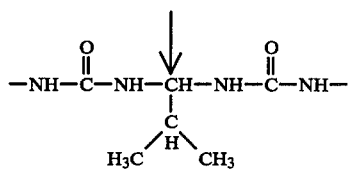

as linking elements within the fused or added polymethylene urea groups may also advantageously be used as fertilizers. The site indicated by the arrow is considerably more prone to hydrolysis than methylene-linked urea segments. The substances in question may be very effectively used as fertilizers from which nitrogen is released quickly and uniformly over long periods.

Those substances according to the present invention which have been produced using various azulmic acids may also be used with advantage as fertilizers. By virtue of the manifold chemical reactivity and absorbency of the azulmic acids, such products are distinguished by particularly high structural variability. For example, relatively large quantities of acids, preferably phosphoric acid and nitric acid, may be bound. Acids present in excess may be neutralized, for example by gassing with ammonia. Such products are capable of supplying plants both with organically bound and also with inorganically bound nitrogen.

Products which still contain aldehydes, for example formaldehyde, after production are best treated with amines or ammonia before they are used as nitrogen fertilizers. Formaldehyde treated with ammonia, for example, is converted into hexamethylene tetramine which is a very effective nitrogen fertilizer.

In cases where azulmic acids (crude azulmic acids, modified azulmic acids and/or stabilized azulmic acids) are used in the production of the biomasses modified in accordance with the present invention, normally highly water-soluble cell ingredients of the biomasses (such as polysaccharides), water-dispersible or soluble glycolipids, lipoproteins, degraded proteins, nucleic bases, degraded, but uncondensed nucleic acids, may be completely adsorbed onto azulmic acids so that these substances (which are valuable humidifiers and plant nutrients) do not enter the effluent, but instead are available to the plants as nitrogen fertilizers.

Those isocyanate-free products which have been produced from biomasses free from heavy metal salts and rich in proteins and, optionally, physiologically compatible additives may be used as animal feed supplements.

In addition, the modified heavy metal-free biomasses produced in accordance with the present invention are suitable for use as soil improving agents. To this end, it is preferred to use those products, according to the present invention, which contain wood powder or powdered vegetable material. Those modified biomasses usable in accordance with the present invention which have been produced using azulmic acids may also be used with advantage as soil-improving agents.

Those modified biomasses usable in accordance with the present invention which contain fault-rich azulmic acids in bound form have a certain polyelectrolyte character and may act as ion-exchanging nitrogen fertilizers in the soil. In this case, the ions required by the plants, for example, potassium and/or ammonia ions, are given off to the soil or to the substrate, while other ions are bound.

By virtue of the high absorbency and high complex-forming capacity thereof, modified biomasses usable in accordance with the present invention which contain azulmic acids or other compounds capable of complex formation may also be used for fixing harmful substances in soil. For example, it is possible to bind undesirable heavy metal ions present in soil, such as lead and mercury ions, by means of the substances containing azulmic acid usable in accordance with the present invention so firmly that there is no longer danger of plant damage. In addition, oil impurities, overdosages of plant protection agents or excessive salt concentrations in substances may be eliminated by adding such substances suitable for use in accordance with the present invention.

Substances usable in accordance with the present invention which, in addition to other plant nutrients, also contain peat may readily be used for the production of molded peat pots for gardening purposes by the addition of binders, such as starch, degraded celluloses, alginates and pectins. In this case, it is best for the ratio, by volume, of white peat to black peat in the substrate be about 1:1.

Modified biomasses usable in accordance with the present invention which, in addition to nitrogen and other plant nutrients contain from about 20 to 40%, by weight, of peat are also especially suitable for covering soil and substrates and also rows of seeds because the dark color of the substances according to the present invention guarantees a good earth-like appearance, prevents soil encrustation and promotes quicker germination of the seeds.

Peat-containing substances usable in accordance with the present invention are also suitable for preventing or reducing the release of odors during decomposition processes.

Substances useable in accordance with the present invention which, in addition to other plant nutrients, also contain peat may be converted by the addition of starch adhesives, hemi-celluloses or alginates into shaped, air-permeable and moisture-retaining materials which are suitable for use as packaging material for transporting plants.

The substances usable in accordance with the present invention may be used either as such or in formulations for supplying plants with nitrogen and, optionally, other nutrients and also as soil-improving agents.

In this respect, the substances usable in accordance with the present invention may be converted into the conventional formulations, such as emulsions, spraying powders, suspensions, powders, dusting agents, foams, pastes, granulates, suspension-emulsion concentrates, seed powders, natural and synthetic substances impregnated with active principles or microencapsulations in polymeric substances and in coating compositions for seeds.

These formulations are produced in known manner, for example by mixing the active ingredients with diluents (i.e., liquid solvents), and/or solid carrier substances, optionally using surface-active agents (i.e., emulsifiers, and/or dispersants and/or foam-forming agents). Where water is used as the diluent, it is also possible, for example, to use organic solvents as auxiliary solvents. Suitable liquid solvents are, in general, aromatic hydrocarbons (such as xylene, toluene, or alkyl naphthalenes), chlorinated aromatic or aliphatic hydrocarbons (such as chlorobenzenes, chloroethylenes or methylene chloride), aliphatic hydrocarbons (such as cyclohexane or paraffins, for example petroleum fractions), alcohols (such as butanol or glycol), and ethers and esters thereof, ketones (such as acetone, methyl ethyl ketone, methyl isobutyl ketone or cyclohexanone), strongly polar solvents (such as dimethyl formamide, dimethyl sulfoxide, and water). Suitable solid carrier materials are natural powdered minerals (such as kaolins, aluminas, talcum, chalk, quartz, attapulgite, montmorillonite or diatomaceous earths), and synthetic powdered minerals (such as highly disperse silica, aluminum oxide and silicates). Suitable solid carrier materials for granulates are broken and fractionated natural minerals (such as calcite, marble, pumice, sepiolite, dolomite and synthetic granulates of inorganic and organic powders) and granulates of organic material (such as sawdust, coconut shells, corn cobs and tobacco stalks). Suitable emulsifiers and/or foam-forming agents are non-ionic and anionic emulsifiers, such as polyoxyethylene fatty acid esters, polyoxyethylene fatty alcohol ethers (for example, alkyl aryl polyglycol ether), alkyl sulfonates, alkyl sulfates, aryl sulfonates and protein hydrolysates. Suitable dispersants are, for example, lignin sulfite waste liquors and methyl cellulose.

Adhesives, such as carboxymethyl cellulose, natural and synthetic polymer powders, granulates or latices, such as gum arabic, polyvinyl alcohol and polyvinyl acetate, may also be used.

Dyes (such as inorganic pigments, for example, iron oxide, titanium oxide and Prussian blue), and organic dyes (such as alizarin dyes and azometal phthalocyanine dyes), and trace nutrients (such as salts of iron, manganese, boron, copper, cobalt, molybdenum and zinc), may also be used.

The formulations generally contain from 0.1 to 95%, by weight, preferably from 0.5 to 90%, by weight, of active ingredient.

The substances according to the present invention may be present in the formulations in admixture with other fertilizers or pesticides.

They may be applied by the methods normally used in agriculture and horticulture, i.e., for example by direct introduction into soil, by pouring, spraying, scattering, dusting, etc. Specialized forms of application include root application, leaf application, stalk injection and bark application. In the case of root application, the fertilizer may either be mixed with the substrate used for cultivation or may be introduced into furrows in the ground. In addition, the fertilizer may be introduced into the deeper root zones by means of a so-called "fertilizer lance" and also through punched or drilled holes.

The quantity in which the substances according to the present invention are used may be varied within relatively wide limits. Where the substances according to the present invention are used as a fertilizer or soil-improving agent, the quantity in which they are used is essentially determined by the type of soil and also by the nutrient demand of the particular plants. In general, the active ingredient is used in quantities of from 0.1 to 200 kg/ha, preferably from 1 to 100 kg/ha. Where the substances according to the present invention are used for other purposes, for example, for covering substrates, for the production of packaging materials for plants, for protecting plants or parts of plants, for the production of molded peat pots or for binding undesirable odoriferous substances, the quantity in which the active ingredient is used is adapted to the particular demand.

The dried and powdered polyaddition products of denatured biomasses, isocyanates and, optionally, additives produced in accordance with the present invention are especially suitable for use as a reactive filler for a variety of polyaddition, polycondensation and/or polymerization reactions, particularly where they contain free isocyanate groups, for which they may be used in a quantity of from 2 to 95%, by weight, preferably from 10 to 70%, by weight, and, in particular, from 15 to 40%, by weight, based on the total quantity of modified plastic. (The use as a filler for polyurethane plastics is covered by a co-pending Application filed by the present Applicants and does not form part of the present invention).

As mentioned above, certain coated denatured biomass powders may be used directly (i.e. without additional binder) as heat-formable molding compositions.

The powders obtained in accordance with the present invention are preferably incorporated as filler in aminoplast and phenoplast resins. In this case they are advantageously present during the actual production of these resins in known manner from carbonyl compounds (particularly formaldehyde) and aminoplast or phenoplast monomers (preferably urea, melamine and/or phenol) and are chemically incorporated into the polymer during its formation through the numerous reactive groups thereof. Carbonyl compounds and aminoplast or phenoplast monomers suitable for this purpose are described, for example, in German Offenlegungsschriften Nos. 2,324,134; 2,639,254 and 2,713,198.

The biomasses worked-up in accordance with the present invention may also be used as a reactive component in the production of epoxide resins.

Isocyanate groups present in the modified biomass may react both with the hydroxyl groups (present in epoxide resins) and also, at elevated temperatures, preferably above 160° C., with the epoxide groups to form oxazolidone rings.

The powdered modified biomasses are preferably mixed homogeneously with liquid diepoxides at room temperature or elevated temperature and reacted under known process conditions, optionally in the presence of a hardener (for example, an amino compound, dicarboxylic acid or dicarboxylic acid anhydride). In numerous cases (particularly at hardening temperatures above 100° C., as mentioned above), the polyfunctional biomasses may partly react both with the epoxide resin and also with the hardener during the epoxide polyaddition reaction so that the reactive filler is incorporated into the hardened cast resin by main valency bonds.

The biomasses added in total quantities of up to about 50%, by weight, based on the end product, reduce in particular the inflammability of the resins produced from epoxides and, in addition, restrict shrinkage. In the case of large castings, the increase in temperature which occurs internally during hardening is lower than that which occurs in the case of unfilled castings.

However, the biomasses worked-up in accordance with the present invention may also be used as a reactive filler in the production of cyanate resins, for example from the starting compounds described in German Offenlegungsschrift No. 2,260,487.

Biomasses into which optionally copolymerizable, unsaturated groups have been introduced may also be used with advantage in the production of plastics in known manner by the polymerization or copolymerization of monomers containing olefinically unsaturated groups. Examples of such monomers are acrylonitrile, styrene, butadiene, acrylic acid, methacrylic acid, vinyl chloride, vinyl acetate and unsaturated polyesters. The polymerization reactions are preferably carried out in a liquid medium, for example in water or an organic solvent, in the presence of the very finely divided biomasses.

The modified biomasses optionally containing free NCO groups produced in accordance with the present invention may readily be coated by polymerization reactions in which monomeric or oligomeric vinyl compounds are (co)polymerized in the presence of the finely ground biomasses, optionally in a solvent which is inert to isocyanate groups.

The biomasses worked-up in accordance with the present invention are also particularly important as binders or as fillers in the production of boards or moldings in hot presses by binding lignocellulose-containing fibers, chips or layers. In this case, additional binders are preferably the condensation products of formaldehyde with urea, melamine or phenol known for this purpose, particularly in the form of aqueous solutions or dispersions thereof. It is known from German Offenlegungsschrift No. 1,669,759 and from German Auslegeschrift No. 1,653,169 that polyisocyanates may also be used instead of or in addition to such binders in the production of molded materials based on vegetable lignocellulose-containing starting materials.

It has now been found that the biomasses modified in accordance with the present invention are eminently suitable for this purpose (above all where they contain free NCO groups or where additional isocyanates are used). In this case, they are used in a quantity of from 2 to 90%, by weight, preferably from 10 to 60%, by weight, based on the total weight of the molding.

Suitable lignocellulose-containing starting materials which may be bound in this way are, for example, wood, bark, cork, bagasse, straw, flax, bamboo, alfa grass, rice husks, sisal and coconut fibers. The material may be in the form of granulates, chips, fibers or powder and may have a water content of from 0 to 35%, by weight, preferably from 5 to 25%, by weight. From 1 to 50%, by weight, preferably from 5 to 20%, by weight, of a polyisocyanate and/or a formaldehyde resin (expressed as solids, based on the total weight of the molding) and the above-mentioned quantity of modified biomass are added to it, followed by pressing (generally under the effect of heat and pressure) to form panels or moldings.

Laminated panels or moldings may also be produced in the same way from veneers, papers or fabrics. Laminated boards or moldings may also be produced in this way from veneers and strip-form, bar-form or rod-form center layers (so-called "cabinet making boards") by treating the veneers as described above with the modified biomass and, optionally, the conventional binder and subsequently pressing them with the center layers, generally at elevated temperature and pressure. In this connection, it is preferred to apply temperatures from 100° to 250° C. and, in particular, from 130° to 200° C. The initial pressure applied is preferably from 5 to 150 bars. The pressure subsequently falls, generally towards zero, in the course of the pressing operation. It is, of course, also possible to use known organic or inorganic fungicides, insecticides or flameproofing agents in quantities of from about 0.05 to 30%, by weight, preferably from 0.5 to 20%, by weight.

Accordingly, the present invention also relates to a process for the production of panels or moldings by the hot pressing of lignocellulose-containing starting materials which is characterized in that from 2 to 90%, by weight, based on the total weight of the molding, of the biomasses modified in accordance with the present invention and, optionally, conventional formaldehyde resins are used as binder.

The biomasses worked-up in accordance with the present invention may also be generally added as reactive filler to lacquers and coatings of various types (in quantities of from about 2 to 70%, by weight, preferably from 5 to 40%, by weight, based on the total solids content). Examples of such lacquers and coatings are roof or floor coverings, gap-filling and surfacing compounds, optionally using bitumen or tar compositions. Another potential application is in the modification of thermoplastic plastics. In this case, the biomasses are mixed with the thermoplast in a quantity of from 3 to 200%, by weight, preferably from 10 to 100%, by weight, based on thermoplast, using known techniques (for example co-extrusion) and the resulting mixture optionally subjected to thermoplastic forming, for example by injection molding or pressmolding.

Materials of this type may be used, for example, in the production of structural components or furniture.

The present invention is illustrated by the following Examples in which the quantities quoted represent parts and percentages by weight, unless otherwise indicated.

A from 7 to 12% aqueous surplus activated sludge ("BS"), which had been formed by the multiplication of microorganisms, particularly bacteria, fungi, and protozoae, from industrial and communal effluents in a fully biological purification plant and obtained by centrifuging a clarified sludge originally containing approximately 1%, by weight, of organic matter, was used as the biomass in Examples 1 to 15 below. The surplus activated sludge parts used had a gel-like character, could not be filtered and, even in the fresh, biologically still active state, gave off an unbearable odor. On standing, the untreated biomass putrefied in a few days, giving off gases. The dry mass had a nitrogen content of from 7.8 to 8.5%, by weight, and an ignition loss of from 81 to 87%, by weight.

In practice, these surplus aqueous purified sludges are mixed with inorganic primary sludges in from the same to twice the quantity, based on solids, in the purification plant in order to make them filterable, filtered in filter presses to form an approximately 50% filter cake and transported to dumps.

Examples 1 to 12 below illustrate the working-up of the biomasses by isocyanate polyaddition in aqueous or organo-aqueous, disperse phase. Formulations and test results are shown in Table 1.

TABLE I

| Example | Biomass Conc. 1 | Type 2 | pH 3 | Isocyanate 4 | Solvent 5 |
|---|---|---|---|---|---|
| 1 | 12.1 | BSD | 1.4 | 10 Bz | 5 Ac |
| 2 | 12.1 | BSD | 1.9 | 10 Tl | 5 Ac |
| 3 | 12.1 | BSD | 6.5 | 10 H | 30 Ac |
| 4 | 12.1 | BSD | 2.8 | 10 D 44 | 30 Ac |
| 5 | 6.7 | BSA | 2.5 | 50 D 44 V 20 | 5 Ac |
| 6 | 6.7 | BSA | 3.5 | 100 T 80 | 30 To |
| 7 | 11.4 | BSA | 6.8 | 100 T 80-R1 | 5 Ac |
| 8 | 12.1 | BSD | 1.7 | 100 T 80-R2 | 20 Ac |
| 9 | 11.4 | BSA | 6.8 | 100 T 80-R2 | 10 To |
| 10 | 11.4 | BSA | 3.0 | 200 T 80-R2 | 5 Ac |
| 11 | 12.1 | BSD | 1.7 | 100 T 80-R3 | 10 To |

| Example | Dry Mass %, by weight 6 | Nitrogen 7 | Odor 8 |
|---|---|---|---|
| 1 | 25 | 7.5 | slight |
| 2 | 26 | 7.4 | slight |
| 3 | 41 | 11.2 | very slight |
| 4 | 42 | 8.3 | very slight |
| 5 | 37 | 8.7 | very slight |
| 6 | 49 | 12.2 | none |
| 7 | 35 | 12.5 | none |
| 8 | 51 | 12.6 | very slight |
| 9 | 45 | 12.7 | none |
| 10 | 48 | 14.2 | none |
| 11 | 39 | 12.8 | none |

Explanation of Table 1

Column 1: Concentration of the aqueous surplus activated sludge (BS) used in percent, by weight.

Column 2: Type of surplus activated sludge used:
 BSA=biologically fully activated, i.e. centrifuged BS run off fresh from the settling tank in the form of a 1% sediment. Viscosity at 25° C.: 580 cP.
 BSD=biologically deactivated BS. The BS was denatured by refluxing for 2 hours with 2.5%, by weight, of a 38% aqueous formaldehyde solution at pH from 6.5 to 7, the biomass being partially hydrolyzed.
 BSA and BSD are unfilterable starting materials.

Column 3: pH=pH value during the isocyanate polyaddition reaction; the end products are each adjusted to pH from 6 to 7.

Column 4: Parts, by weight, of isocyanate, based on 100 parts of BSA or BSD-solids.
 Bz=benzyl isocyanate
 T1=4-tolyl isocyanate
 H=1,6-hexamethylene diisocyanate
 D44 =4,4'-diphenyl methane diisocyanate (pure)
 D44V20=Technical crude phosgenation products of an aniline/formaldehyde condensate; NCO-content: 29%.
 T80=2,4-/2,6-tolylene diisocyanate; monomer mixture in a ratio of 80:20.

The isocyanates T80-R1, R2 and R3 are granulated isocyanate residue slags from the commercial production of 2,4-/2,6-tolylene diisocyanate (isomer ratio: 80:20) which were obtained in accordance with German Offenlegungsschrift No. 2,846,815 or U.S. Pat. No. 4,297,456 by denaturing the NCO-containing, from about 150° to 200° C., viscous tar-like sump phase (distillation residue) with from about 4 to 5 times the quantity of water and which, depending on the drying temperature (from 40° to 70° C.), have the indicated residual isocyanate content which was determined in acetone at 50° C.
 T80-R1 NCO-content: 14.2%; particle size 20–250 μm
 T80-R2 NCO-content: 9.9%; particle size 30–500 μm
 T80-R3 NCO-content: 5.0%; particle size 100–800 μm Column 5: Parts, by weight, of solvent, based on 100 parts of the aqueous surplus activated sludge used.
 Ac=Acetone; Tol=toluene.

Column 6: Percent, by weight, of dry mass in the filter cake after removal of the water and solvent by filtration under suction.

Column 7: Nitrogen content of the dry mass in percent, by weight.

Column 8: Odor qualification of the product produced in accordance with the present invention.

Comparison Tests

When the activated sludges mentioned in Column 2 were exposed to the process and reaction conditions according to the present invention, as described in the following, but without the addition of the monoisocyanates, diisocyanates or higher polyisocyanates mentioned, the unbearable odor persisted in the case of BSD and, in the case of BSA, was considerably intensified on storage with vigorous evolution of gas (inter alia elimination of hydrogen sulfide), so that spreading as a plant nutrient, for example, was impossible. Process and reaction conditions for Examples 1 to 11 and the Comparison Tests without isocyanate polyaddition:

The surplus activated sludge was introduced at room temperature into a vessel of VA steel equipped with a reflux condenser, after which the quantity of monoisocyanate or polyisocyanate indicated in Table 1 was stirred in. The solvent was either combined with the isocyanate before the addition(Examples 1 to 4) or separately introduced ( Examples 5 to 11). The contents of the vessel were heated under reflux to boiling point and maintained at boiling temperature for from 1 to 3 hours. Where an acid pH value is indicated in Table 1, it was adjusted with sulfuric acid, generally before the isocyanate was added. When no more free isocyanate could be detected, the contents of the vessel were neutralized with sodium triphosphate or alkali metal hydroxide and, after cooling, were compressed in a conventional pressure filter or filter press. To reduce the water content, the moist filter cake was dried in a recirculating air heating cabinet (Examples 1 to 8,9 and 11) or by spreading out in air (Examples 7 and 10) until the required water content was reached. Where the product is to be used as an odorless long-term fertilizer for horticultural and agricultural purposes, it is preferably dried to a water content of from about 10 to 40%, by weight, and reduced to a grain size of from 1 to 4 mm.

EXAMPLE 12

2000 parts of a 12.1%, deactivated aqueous sludge, 10 parts of an emulsifier of 1 mole of oleyl alcohol and 400 moles of ethylene oxide and 242 parts of the powdered tolylene diisocyanate residue tar T80-R2 were thoroughly mixed and the resulting mixture heated for 1 hour to 145° C. in a pressure vessel. After cooling, the mixture was filtered under suction. The moist filter cake had a solids content of 38%. The odorless dry mass had a nitrogen content of 12.7%.

Examples 13 to 15 below describe the production of biomass polyaddition-polycondensation products in accordance with the present invention simultaneous isocyanate polyaddition and aminoplast condensation reactions in aqueous-organic phase.

EXAMPLE 13

Formulation:

880 parts, by weight, of an 11.4%, aqueous biologically fully active purified sludge adjusted to pH 2.1 using sulfuric acid, 100 parts, by weight, of powdered tolylene diisocyanate residue slag T80-R2 having an NCO content of 9.9%;

40 parts, by weight, of a 30% aqueous formaldehyde solution, 30 parts, by weight, of urea and 100 parts, by weight, of toluene.

Reaction conditions:

The above-mentioned components were combined at room temperature in a stirrer-equipped vessel provided with a reflux condenser and heated with stirring to the boiling temperature. The mixture was then refluxed for from about 2 to 3 hours until no more free isocyanate could be detected. It was then neutralized with calcium hydroxide solution until the pH remained constant at 6.5 to 7. After cooling, the mixture was compressed in a pressure filter at from 0.5 to 2 bars.

The odorless filter cake had a solids content of 47%. The dry mass had a nitrogen content of 18.4%.

EXAMPLE 14

The procedure is as in Example 13, except that 10 parts of monomeric tolylene diisocyanate (2,4-/2,6-isomer=80:20) were used instead of 100 parts of isocyanate residue slag.

An odorless filter cake having a solids content of 34% was obtained under the same reaction conditions.

The nitrogen content amounted to 19.1%, based on dry mass.

EXAMPLE 15

Formulation:

880 parts, by weight, of the same 11.4% surplus activated sludge as in Example 13, 100 parts, by weight, of black powdered azulmic acid produced by the polymerization of hydrocyanic acid in accordance with German Offenlegungsschrift No. 2,806,019 or U.S. patent application Ser. No. 11,542, 20 parts, by weight, of a 30% aqueous formaldehyde solution, 100 parts, by weight, of 4,4'-diphenyl methane diisocyanate and 100 parts, by weight, of acetone.

The reaction took place under the conditions described in Example 13. The NCO-free odorless filter cake had a solids content of 56.5% and a nitrogen content of 21.2%, based on dry substance.

Foul-smelling surplus activated sludge powders dried at about 110° C. were used as biomass in Examples 16 to 27 below. These surplus activated sludge powders, which emanate from fully biologically, industrial and communal purification plants, are normally stored in dumps or, in rare cases, are burned. Once they had become moist, these activated sludge powders underwent biological reactivation in a few days and continued to putrefy, giving off an increasingly intense odor.

In the following Examples, these biomasses were denatured in accordance with the present invention by isocyanate polyaddition in predominantly organic, disperse phase or simply wetted with organic solvents. Formulations and test results are shown in Table 2.

TABLE 2

| Example | Process | Isocyanate | Solvent Additions | |
|---|---|---|---|---|
| 1 | 2 | 3 | 4 | 5 |
| 16 | I | 200 T 80 | 100 Tol | — |
| 17 | I | 200 T 80 R2 | 100 Tol | — |
| 18 | I | 100 T 80 R3 | 80 Tol | — |
| 19 | I | 100 T 80 R2 | 80 Ac | 100 Az |
| 20 | I | 100 D 44 | 80 Ac | 100 Az |
| 21 | I | 50 D 44 | 100 Ac | — |
| 22 | I | 50 H | 100 Ac | — |
| 23 | I | 50 IPDI | 100 Ac | — |
| 24 | I | 50 L | 100 Ac | — |
| 25 | II | 50 D 44 | 25 Ac | — |
| 26 | II | 100 T 80 R2 | 20 Tol | — |
| 27 | II | 100 T 80 R2 | 25 Ac | 20 Uro |
| 28 | III | 100 T 80 R3 | — | — |
| 29 | I | 100 T 80 R2 | 100 Ac | 100 ABS |

| | Dry mass | | |
|---|---|---|---|
| Example 1 | Nitrogen 6 | Odor 7 | NCO content 8 |
| 16 | 13.7 | none | 3.5 |
| 17 | 11.3 | none | 0 |
| 18 | 13.0 | none | 0 |
| 19 | 23.4 | none | 0 |
| 20 | 21.3 | none | 0 |
| 21 | 9.3 | none | 0 |
| 22 | 11.0 | none | 0 |
| 23 | 10.3 | none | 0 |
| 24 | 9.2 | none | 0 |
| 25 | 9.3 | none | 0 |
| 26 | 12.8 | none | 0 |
| 27 | 15.5 | none | 0 |
| 28 | 12.8 | none | 0 |
| 29 | 9.7 | none | 0 |

Explanation of Table 2

Column 1: Example No.
Column 2: Process used (see following description)
Column 3: Diisocyanates and isocyanate residue slags as explained in Table 1 (parts, by weight, based 100 parts, by weight, of surplus activated sludge powder). T80=tolylene diisocyanate (80% 2,4-; 20% 2,6-isomer).
IPDI=Isophorone diisocyanate L=Tris-urethane isocyanate of 1 mole of 1,1,1-trimethylol propane and 3 moles of 2,4-tolylene diisocyanate (used in the form of a 75% solution in ethyl acetate).

Column 4: Solvent in parts, by weight, based on total solids.
Ac=acetone; Tol=toluene.

Column 5: Additions (parts, by weight, based on 100 parts, by weight, of surplus activated sludge powder)
Az=Azulmic acid produced by the polymerization of hydrocyanic acid in accordance with German Offenlegungsschrift No. 2,806,019 or U.S. patent application Ser. No. 11,542 (particle size: 10–100 μm),
Uro=Urotropin in the form of a 30% solution in water (with a catalytic quantity of sulfuric acid),
ABS=Graft copolymer of butadienestyrene-acrylonitrile; added in the form of a 33% aqueous dispersion.

Column 6: Nitrogen content of the dry mass in percent, by weight.
Column 7: Odor qualification of the product produced in accordance with the present invention.
Column 8: NCO content of the dried process products.

Process and Reaction Conditions for Examples 16 to 27

Process I:
The components combined at room temperature in a stirrer-equipped vessel provided with a reflux condenser were heated with stirring for from 2 to 4 hours to boiling temperature until the NCO-content remains constant (Example 16) or is zero (in the other Examples).

The solvent was either completely distilled off with stirring, in which case the temperature was increased by 30° to 40° C. towards the end and the powderform process products were discharged from the vessel under excess pressure or pneumatically removed therefrom, or the biomass polyaddition products dispersed in the organic medium were allowed to cool, the dispersant was filtered off and the product subsequently dried.

Process II:
(a) Batch embodiment:
The components mentioned in Table 2 were wetted with the small quantity of acetone or toluene indicated in a kneader and heated for from 30 to 90 minutes to from 110° to 140° C. in a pressure vessel under the autogenous reaction pressure. Upon completion of the isocyanate polyaddition reaction, the reaction mixture was left to cool to about the boiling temperature of the solvent which was then quantitatively distilled off.

The products were isolated cold in the form of odorless, sterile powders which no longer putrefied, even on moistening with water and prolonged storage. (b) Continuous embodiment (preferred):

With the same result, the reaction components were introduced into a twin-screw evaporation extruder, with toluene as the wetting agent, in which the isocyanate polyaddition reaction was carried out over a period of from 10 to 30 minutes at from 140° to 170° C. Before the powder-form products emerged from the extruder, the wetting agent was completely recovered by distillation.

Process III (particularly preferred):
The powder-form starting compounds were continuously introduced into a fluidized bed and reacted for an average of from 10 to 20 minutes at a temperature of from 145' to 180° C. The odorless activated sludge residue polyisocyanate polyaddition product was continuously removed from the reactor by forced upward flow.

EXAMPLE 28

1000 g of a bacterial activated sludge (solids content approximately 8.5%) emanating from a fully biological purification plant for industrial and communal effluents and consisting of a variety of microorganisms with traces of the following plant protection agents (herbicides):
N-methyl isopropyl carbamate (0.5 g)
4-amino-6-t-butyl-3-methyl thio-4,5-dihydro-1,2,4-triazine-5-one (0.5 g)
N-(3-benzthiazolyl)-N,N'-dimethyl urea (0.5 g),
were initially heated with intensive stirring to 80° C. with 100 g of 30% formalin (1 mole) and 25 g of 85% phosphoric acid in a ground glass flask. The cell walls of the bacteria were thus ruptured and the plant protection agents present deactivated and hydrolyzed by reaction of the NH$_2$- or NH-functions thereof with formaldehyde by N-methylolation (>N—CH$_2$—O—H$_2$-N>) or methylene linkage (>N—CH$_2$—N<). After this primary reaction, samples were taken and centrifuged. By titrating the formaldehyde in the filtrates, it was analytically determined that 0.05 mole of formaldehyde has been consumed. A solution of 60 g of urea (1 mole) in 100 g of water and 10 g of 30% formalin (0.1 mole) were then added to the reaction mixture. After condensation for 15 minutes at 70° C., the mixture was cooled over a period of 30 minutes to a temperature of 45° C. and a readily filterable, powder-form biomass mixed condensate was obtained. This biomass mixed condensate was neutralized with calcium hydroxide, as a result of which substantially insoluble calcium phosphate precipitated in very finely divided form in the biomass condensate dispersion. The powder-form product was filtered off and washed with a 2% aqueous ammonia solution. The product was then dried under reduced pressure at 70° C., giving a substantially odorless powder in an amount of 176 g. The nitrogen content amounted to 13.4%.

Based on the mixture of condensed proteins, enzymes nucleic acids and other cell ingredients, the process product contained about 39%, by weight, of polymethylene ureas having the following idealized constitution:

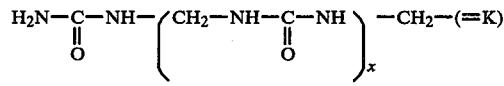

wherein x is unknown and the fraction of (K) fused to functional groups of the biomass could not be analytically determined on account of the insolubility of the biomass mixed condensate.

100 g of the dried product were mixed with 20 g of hexamethylene diisocyanate and 100 g of toluene and the resulting mixture maintained for 6 hours at 150° C. in a pressure vessel. It was then washed with methanol. 106 g of a biomass isocyanate polyaddition product which was completely odorless and sterile were obtained after drying.

EXAMPLE 29

Quantities of 1000 g of a bacterial activated sludge (dry matter content approximately 8.4%) emanating from a fully biologically purification plant for industrial and communal effluents were methylolated or condensed for 10 minutes at 70° C. with 1 mole of formaldehyde (100 g of 30% formalin), followed by the addition of each of the following isocyanates which, were reacted with the reactive groups of the biomass or with water, to form in situ polyurea derivatives which immediately co-condensed with the formaldehyde (0.85 mole) and N-methylol compounds of proteins still present following the addition of 16 g of concentrated sulfuric acid:

(a) 0.2 mole of 2,4-tolylene diisocyanate dissolved in 40 g of acetone,
(b) 0.2 mole of hexamethylene diisocyanate dissolved in 40 g of acetone,
(c) 0.2 mole of 4,4'-diisocyanatodiphenyl methane dissolved in 40 g of acetone,
(d) 0.2 mole of lysine ester methyl isocyanate dissolved in 40 g of acetone,
(e) 44 g of a tolylene diisocyanate residue isocyanate having an NCO content of 16.2%, by weight, dissolved in methylene chloride,
(f) 40 g of a higher polyisocyanate of aniline formaldehyde condensates dissolved in 40 g of acetone,
(g) 0.4 mole of methoxy methyl isocyanate,
(h) 34 g of biuret polyisocyanates (dissolved in 40 g of acetone) based on hexamethylene diisocyanate having an NCO content of 22.3%, this mixture contained approximately 33%, by weight, of triisocyanatohexyl biuret having the following idealized constitution

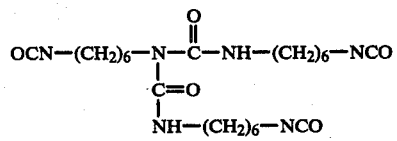

in addition to biuret polyisocyanates of higher molecular weight and polyisocyanato-polybiurets,
(i) 48 g of uretone imine triisocyanate (dissolved in 40 g of acetone) corresponding to the following idealized formula:

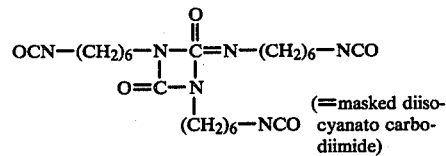

(j) 42 g of the following idealized tris-urethane triisocyanate

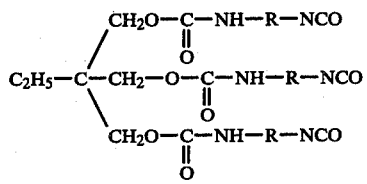

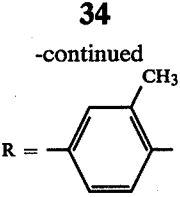

dissolved in 80 g of acetone.

The particular isocyanate added reacted with the biomass or with the water to form polyureas of relatively high molecular weight which contained highly reactive terminal $NH_2$-groups and numerous NH-groups which co-condensed with the formaldehyde present and the resulting N-methylol compounds or N,N-aminals of the proteins and cell ingredients. The reaction mixture was then neutralized using calcium hydroxide and washed with 2% aqueous $NH_3$-solution.

In the case of reactions (a) to (i) readily filterable biomass mixed condensates were obtained. Yields:
(a) 120 g, N-content: 8.6%, calcium sulfate content: 12.8%
(b) 116 g, N-content: 9.4%
(c) 140 g, N-content: 7.9%
(d) 120 g, N-content: 9.1%
(e) 139 g, N-content: 8.5%
(f) 132 g, N-content: 8.5%
(g) 118 g, N-content: 7.8%
(h) 141 g, N-content: 11.6%
(i) 123 g, N-content: 9.8%

0.1 mole of ethylene glycol, diethylene glycol, 1,4-butane diol or water-immiscible diols, such as hexane diol and 2-ethyl-1,3-hexane diol, may be added to the aqueous starting biomass dispersion, resulting in the formation not only of polyureas, but also of polyurethane segments which, through the high NH-content thereof, again contain functional groups for co-condensation with the aldehydes and the methylol groups of the proteins and N-methylolated cellular constituents of the biomass.

The powder-form filtered biomass mixed condensates obtained were quantitatively freed from traces of formaldehyde by heating to 50° C. in 2% ammonia solution, resulting in the formation of water-soluble hexamethylene tetramine, and were obtained in the form of completely odorless powders after extraction with acetone. Even after storage for lengthy periods, these powders remained odorless because the entire enzyme spectrum of the biomasses was completely deactivated.

What is claimed is:

1. A process for the production of denatured polyaddition products of biomasses and isocyanates, comprising reacting
   (A) from 5 to 98%, by weight, based on (A)+(B), of a biomass based on microorganisms or derivative and decomposition products thereof with
   (B) from 95 to 2%, by weight, based on (A)+(B), of a compound containing isocyanate groups, at temperatures of at least 50° C. with complete denaturing of component (A) wherein said biomass is further reacted with a carbonyl compound, a compound capable of aminoplast or phenoplast formation, or mixtures thereof, before, after, or during said isocyanate polyaddition reaction.

2. The process of claim 1, wherein said carbonyl compound is formaldehyde.

3. The process of claim 1, wherein said biomass is dispersed in water and has a solids content of 0.3 to 20%, by weight.

4. The process of claim 3, wherein 3 to 80%, by weight, based on the dry weight of (A)+(B) of component (B) is used.

5. A process for the production of denatured polyaddition products of biomasses and isocyanates, comprising reacting
 (A) from 5 to 98%, by weight, based on (A)+(B), of a biomass based on microorganisms or derivative and decomposition products thereof with
 (B) from 95 to 2%, by weight, based on (A)+(B), of a compound containing isocyanate groups, at temperatures of at least 50° C. with complete denaturing of component (A)
wherein said compound containing isocyanate groups comprises a substantially monomer-free, cross-linked distillation residue having a NCO content of from 1 to 15%, by weight, and a particle size of less than 2 mm which is insoluble in inert organic solvents and cannot be melted without decomposing and which has been obtained by (a) removing the monomeric tolylene diisocyanate from the crude phosgenation product of tolylene diamine, and (b) grinding the residue, wherein said reaction is carried out at 70° to 200° C.

6. The process of claim 5, wherein said distillation residue is reacted with a carbonyl compound or a compound containing Zerewitinoff-active hydrogen atoms.

7. The process of claim 5 in which the compound containing isocyanate groups from which monomeric tolylene diisocyanate has been removed is introduced at a temperature above 150° C. into water prior to grinding.

* * * * *